United States Patent [19]

Troutner et al.

[11] Patent Number: 5,442,969

[45] Date of Patent: Aug. 22, 1995

[54] FLUID SAMPLING MODULE

[75] Inventors: Vernon H. Troutner, St. Petersburg; Andrew D. Hopping, Largo, both of Fla.; Prakash Keshaviah, Plymouth, Minn.

[73] Assignee: Baxter International Inc., Deerfield, Ill.

[21] Appl. No.: 349,126

[22] Filed: Dec. 1, 1994

Related U.S. Application Data

[63] Continuation of Ser. No. 960,088, Oct. 13, 1992, abandoned.

[51] Int. Cl.$^6$ ............... G01N 27/30; G01N 27/46; G01N 3/14
[52] U.S. Cl. ............... 73/863.71; 73/863.02; 73/863.83; 73/863.85; 73/864.14; 73/864.21; 73/864.59; 73/864.65; 73/864.74
[58] Field of Search ........... 73/863.02, 863.23, 863.71, 73/863.83, 863.85, 864.14, 864.21, 864.59, 864.65, 864.74

[56] References Cited

U.S. PATENT DOCUMENTS

| | | | |
|---|---|---|---|
| 2,950,716 | 8/1960 | Bellamy, Jr. et al. | 73/863.86 |
| 4,112,768 | 9/1978 | Holland et al. | 73/422 R |
| 4,224,163 | 9/1980 | Goldhaber et al. | 210/321.74 |
| 4,244,787 | 1/1981 | Klein et al. | 204/1 T |
| 4,412,916 | 11/1983 | Kell | 96/219 |
| 4,508,622 | 4/1985 | Polaschegg et al. | 210/96.2 |
| 4,686,479 | 8/1987 | Young et al. | 324/439 |
| 4,758,337 | 7/1988 | Kohn et al. | 96/219 |
| 4,800,763 | 1/1989 | Hakkers et al. | 73/863.81 |
| 4,865,811 | 9/1989 | Newton et al. | 73/863.71 |
| 4,928,541 | 5/1990 | Toon et al. | 73/864.63 |
| 4,932,987 | 6/1990 | Molina | 96/219 |
| 4,955,857 | 9/1990 | Shettigar | 604/3 |
| 5,024,756 | 6/1991 | Sternby | 210/93 |
| 5,100,554 | 3/1992 | Polaschegg | 210/647 |
| 5,110,477 | 5/1992 | Howard et al. | 210/647 |
| 5,142,271 | 8/1992 | Bailey et al. | 340/606 |

FOREIGN PATENT DOCUMENTS

| | | | |
|---|---|---|---|
| 0437789A2 | 7/1991 | European Pat. Off. | 33/487 |
| 0495412A1 | 7/1992 | European Pat. Off. | A61M 1/16 |
| 0504772A2 | 9/1992 | European Pat. Off. | G01N 33/52 |
| 3436748A1 | 7/1985 | Germany. | |
| 2071846 | 9/1981 | United Kingdom | 73/863.86 |

OTHER PUBLICATIONS

Laurie J. Garred, et al., "Artificial Organs", vol. 16, No. 3, pp. 248-255, 1992; and Abstracts vol. 15, p. 285 No. 4, 1991.
Thomas A. Depner, "Quantitation of Dialysis", vol. 5, No. 2, pp. 147-154, 1992.
E. Klein and J. G. Montalvo, Jr., "International Journal of Artificial Organs", vol. 1, No. 3 pp. 116-122 and No. 4, pp. 175-180, 1978.
"Abstracts of the XII Annual CAPD Conference" vol. 12, Supplement 1, 1992.

*Primary Examiner*—Richard E. Chilcot, Jr.
*Assistant Examiner*—George M. Dombroske
*Attorney, Agent, or Firm*—Thomas S. Borecki; Charles R. Mattenson; Anibal José Cortina

[57] ABSTRACT

A fluid sampling module is provided for utilization in on-line real time fluid monitoring systems. The fluid sampling module can be utilized as a urea input module in a hemodialysis treatment. The hemodialysis monitoring system quantitates the rate and amount of urea removed during the hemodialysis treatment by measuring the urea concentrations as a function of time in the spent dialysate effluent from a hemodialysis machine. The urea input module interfaces with the dialysate effluent waste line from the hemodialysis machine and periodically removes a quantity of the spent dialysate effluent for measurement. The urea input module detects low flow rates and eliminates low flow rate flutter. The urea input module includes a resealable make before break docking interface with the dialysate effluent line and preferably includes a filter between the urea input module and the urea sensor.

48 Claims, 6 Drawing Sheets

FLUID SAMPLING MODULE

This is a continuation of application Ser. No. 07/960,088, filed Oct. 13, 1992, now abandoned).

FIELD OF THE INVENTION

The present invention relates generally to fluid sampling, and more particularly is directed to a flow sensing and fluid sampling module for on line real time monitoring of a fluid process.

BACKGROUND OF THE INVENTION

The fluid sampling module of the invention can be utilized in any type of process, wherein a Newtonian fluid is or can be flowing. Many types of industrial processes require additions of different fluids and it is important and often critical to sample the fluids as they are added to the process. Different types or different concentrations can be added through the same line or a plurality of different lines. To provide proper process control, each fluid should be sampled so that the type, concentration, etc. of the various fluids can be monitored. To effectively sample the fluids, it can be required to obtain the sample from the fluid when it is under at least minimal flow conditions. Therefore, the fluid sampling module of the present invention includes sensing of the fluid flow to ensure that sampling of the fluid only occurs during a period of sufficient fluid flow.

Applicants have discovered a particular use for the fluid sampling module in the hemodialysis treatment, such as performed by hemodialysis machines. Therefore, although the present invention is not limited to a particular fluid or fluid process, for purposes of describing a specific example, the hemodialysis treatment will be described hereinafter in detail.

The use of dialyzer cartridges with hemodialysis machines to remove blood-borne toxins and by-products of metabolism has been conventional for many years. Typically, such a cartridge contains essentially a pair of chambers separated by a semipermeable membrane. Blood is perfused through the first chamber and returned to the patient. The dialysate solution is simultaneously circulated in the opposite direction through the second chamber. A concentration gradient thereby is established which causes waste products carried in the blood to migrate through the semipermeable membrane and into the dialysate solution to form the dialysate effluent.

The principle of hemodialysis has been refined extensively. A number of semipermeable hollow fiber membranes are now utilized in dialyzer cartridges to greatly increase the total membrane surface area to facilitate diffusion across the membrane structure. The hollow fiber membranes include a variety of materials including, for example, cellulose acetate, cellulose triacetate, polyacrylonitrile, polysulfone, and regenerated cellulose, the latter being most commonly used.

One of the most basic considerations in treating a patient with hemodialysis revolves around treatment adequacy. Quite simply, how long should a given patient be dialyzed on a given day. A number of medically adverse effects may result from an inadvertent failure to sufficiently dialyze the patient. At the present time, the average dialysis patient has a life expectancy of only about five years. One reason these patients tend to have a short life expectancy is the deleterious effect of a chronic buildup of various toxins that either are not eliminated at all, i.e. do not pass through the hollow fibers, or are not sufficiently reduced to nontoxic levels. The identity of many of these supposed toxins is not known, although those species known to be eliminated in urine, such as urea, creatinine, phosphate, hydrogen ions, etc. are associated with serious medical consequences when permitted to accumulate in excess of normal levels.

A number of factors can have a substantial effect on treatment adequacy. For example, it is common practice in the field of hemodialysis to reuse the dialysis cartridges. There is technology available for cleaning, disinfecting, or sterilizing used dialysis cartridges, for example, as illustrated in U.S. Pat. No. 4,695,385. Eventually, however, an individual cartridge must be discarded because it loses its dialyzing competency. At the present time, the competency of dialyzers is difficult to assess and therefore often is not rigorously monitored, and a dialyzer cartridge is often not discarded until it visually appears unclean after recleaning, or when fiber bundle volumes or ultrafiltration rates are reduced below a predetermined threshold. It now is known that severe dialyzer dysfunction can occur even when appearance, fiber bundle volume and ultrafiltration rates are normal, as reported by Delmez et al., "Severe dialyzer dysfunction during reuse," *Kidney International*, 35:244 (1989). It is also known that dialyzer competency can not be accurately predicted by the age of the dialyzer cartridge or the number of uses.

Notwithstanding the condition of the dialyzer, one measure of adequacy of dialysis for the individual patient during a given treatment is calculated from the following equation:

$$KT/V \geq 1.0$$

V is an expression of the volume of distribution of urea which is approximately equal to total body fluid volume. V is derived for each individual patient from data such as height, weight and sex. K is the urea clearance of the particular dialyzer in use in milliliters (ml) of blood cleared of urea each minute. T is the treatment time. K is obtained from the typical product insert enclosed with a case of dialyzers and contains a graph of urea clearance versus blood flow rate obtained by random testing of a sample of dialyzers from a particular manufacturing lot. Upon incorporating these values into the above equation, the minimum treatment time can be calculated for a given KT/V value. Other parameters that may be varied to achieve adequate dialysis include blood flow rate, dialysis solution flow rate, dialyzer competency, and temperature.

It has been determined empirically that KT/V values of about 0.8 or greater are associated with low levels of morbidity. See Gotch, L. A., Sargent, J. A. *Kidney International*, 28:526–537, 1985. Even with the use of new dialyzers units there is some risk that a unit selected from a particular lot will have a significantly lower K value than the value indicated in the product insert. The patient receiving treatment from such a dialyzer is therefore at risk of being under-dialyzed. The likelihood of under-dialysis increases upon reuse of the dialyzer cartridge because of the definite but unquantified loss of dialyzer competence with each successive use. Under-dialysis also may occur because of incompetency of access to the patient's circulation. Because of incompetency of the patient's blood access, desired blood flow rates may not be achieved which also can result in underdialysis.

Other parameters than KT/V have also been developed to assess the adequacy of dialysis. Among these are the Urea Reduction Ratio (URR) and Solute Removal Index (SRI). URR is defined as $1-(C_B)_{pre}/(C_B)_{post}$. A good dialysis treatment will have a URR near one (1) while a poor dialysis treatment will have a URR near zero (0). Unfortunately URR does not take into account generation of urea during dialysis, ultrafiltration, or the two pool nature of removal. Consequently SRI has been proposed as a generalized version of URR which does account for these effects. SRI is defined as the amount of the urea removed during a treatment as a fraction of the total body store. Like URR, a good dialysis treatment will have an SRI value near one (1) while a poor dialysis treatment will have an SRI near zero (0). Potentially SRI (unlike KT/V) can indicate the adequacy of a dialysis treatment irrespective of modality (i.e. peritoneal or hemodialysis) and intermittence. Neither URR or SRI however, have been validated as extensively as KT/V as measures of dialysis adequacy.

Although the KT/V, URR and SRI indices are indicative of urea removal and appear to correlate with treatment adequacy, that is not tantamount to saying that urea is a toxic metabolite. There is early literature to suggest that urea is not toxic, per se. However, urea is a major metabolite of protein catabolism and serves as a convenient marker to monitor treatment adequacy.

Urea has a molecular weight of 60 daltons while some of the other protein catabolites may be much larger. It has, therefore, become a subject of controversy whether the relationship between KT/V and morbidity established with the tighter cellulosic membranes is applicable to the more open membranes used for hemofiltration and high flux hemodialysis or to the natural peritoneal membrane.

There is a considerable body of literature on the urea kinetic model. Computer programs, programmable calculators and time-shared computer services have been developed to make urea kinetics more accessible to the dialysis clinician. It has recently been shown (Lindsay, et al, 1989) that KT/V values of less than 0.8 may be associated with a low dietary protein intake that is intractable to nutritional counseling. However, increasing the KT/V to 1.0 or higher, in conjunction with nutritional counseling, is effective in improving dietary protein intake. As low dietary protein intake may be associated with increased morbidity, monitoring of the KT/V and PCR are useful adjuncts to other clinical assessments of the dialysis patient.

Traditional urea kinetics entails numerous measurements and is considered mathematically complex by dialysis clinicians. The various measurements required for accurate kinetic measurements are summarized in Table 1.

TABLE 1

MEASUREMENTS REQUIRED FOR UREA KINETIC CALCULATIONS

Pre dialysis BUN ($C_1$)
Post dialysis BUN ($C_2$)
Pre dialysis BUN for next dialysis ($C_3$)
Dialyzer clearance (K)
Blood flow rate
Arterial BUN
Venous BUN
Dialysate flow rate (effluent) ($Q_{Do}$)

TABLE 1-continued

MEASUREMENTS REQUIRED FOR UREA KINETIC CALCULATIONS

Access recirculation
Peripheral BUN
Residual renal function
Urine volume
Urine concentration
Dialysis duration ($t_d$)
Off dialysis duration ($t_{od}$)
Ultrafiltration rate
Weight gain between dialyses Each of these measurements is associated with finite error and the cumulative effect of these errors may lead to unrealistic urea kinetic parameters.

Prior art hemodialysis machines have not had the capability of in-line monitoring of the hemodialysis treatment. Further, the prior art techniques generally have required the taking of blood samples from the hemodialysis patient.

It thus would be desirable to provide a non-invasive on-line real time monitoring of a fluid process, such as the hemodialysis treatment, while the patient is undertaking the treatment and for example, is attached to the hemodialysis machine. The treatment when based on urea kinetics preferably would require measurements of effluent dialysate concentrations and flow but not of blood samples. The treatment would yield as outputs the KT/V, URR and SRI indices of therapy adequacy, the urea removal and the normalized protein catabolic rate (nPCR), which then could be utilized to assess dietary compliance and adequacy of treatment in real time.

SUMMARY OF THE INVENTION

The present invention is directed to a fluid sampling module for fluid processes. The fluid sampling module can be utilized as a urea input module in on-line real time hemodialysis monitoring systems for hemodialysis machines. The hemodialysis monitoring system quantitates the rate and amount of urea removed during the hemodialysis treatment by measuring the urea concentration in the spent dialysis effluent as a function of time. The fluid sampling urea input module interfaces with the dialysate effluent waste line from the hemodialysis machine and periodically removes a small volume of the spent dialysate effluent for measurement. The urea concentration time profile is determined and analyzed to develop the urea removal, KT/V, URR and normalized protein catabolic rate (nPCR) indices. The fluid sampling module detects the difference between low fluid flow rates, that can indicate the fluid such as dialysate is not in condition to be sampled with normal fluid flow rates. The urea input module includes a resealable docking interface with the dialysate effluent line and preferably includes a filter between the urea input module and the urea sensor.

These and other features and advantages of the invention will be more readily apparent upon reading the following description of a preferred exemplified embodiment of the invention and upon reference to the accompanying drawings wherein:

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENTS

Figure 1:
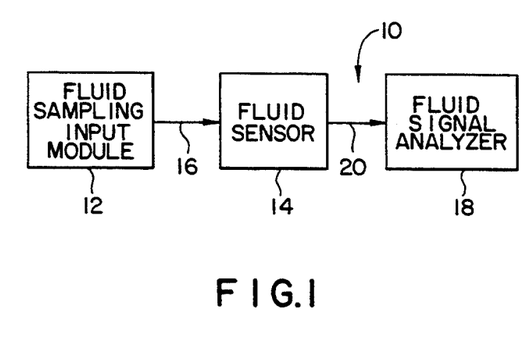
FIG. 1 is a block diagram of one embodiment of a fluid flow monitoring system incorporating the fluid sampling module of the present invention.

Referring to FIG. 1, one embodiment of a fluid flow monitoring system which can incorporate the present invention is designated generally by the reference numeral 10. One preferred monitor 10 for use in a hemodialysis treatment is disclosed and described in application docket number DI 4353, entitled *HEMODIALYSIS MONITORING SYSTEM FOR HEMODIALYSIS MACHINES*, filed concurrently herewith, which is incorporated herein by reference. The monitor 10 can include a fluid sampling input module 12 of the present invention. The fluid sampling module 12 can be utilized with any type of fluid process, such as a hemodialysis treatment, such as in hemodialysis machines produced by the assignee of the present invention, Baxter International Inc. The module 12 samples a volume of the fluid, for example dialysate effluent, intermittently, as desired. The module 12 couples the fluid sample volume to a sensor 14 via a fluid line 16.

The sensor 14 is described herein for example purposes, as a urea sensor. Urea, however, is just one of a number of identifiable constituents generally related to uremia in a patient's blood, which can be utilized as a marker or measure of the effectiveness of the hemodialysis treatment, i.e. the removal of toxins. Such other constituents are, for example, creatinine, uric acid, phosphate, calcium, sodium, potassium, glucose, beta 2 microglobulin, among others. Other types of sensors also can be utilized in the fluid sampling module of the present invention, which sense the required fluid constituent(s) directly or indirectly. The urea sensor 14 generates a signal which is proportional to the urea concentration and electronically couples that signal to a fluid or urea signal analyzer 18 via a line 20.

Figure 2:
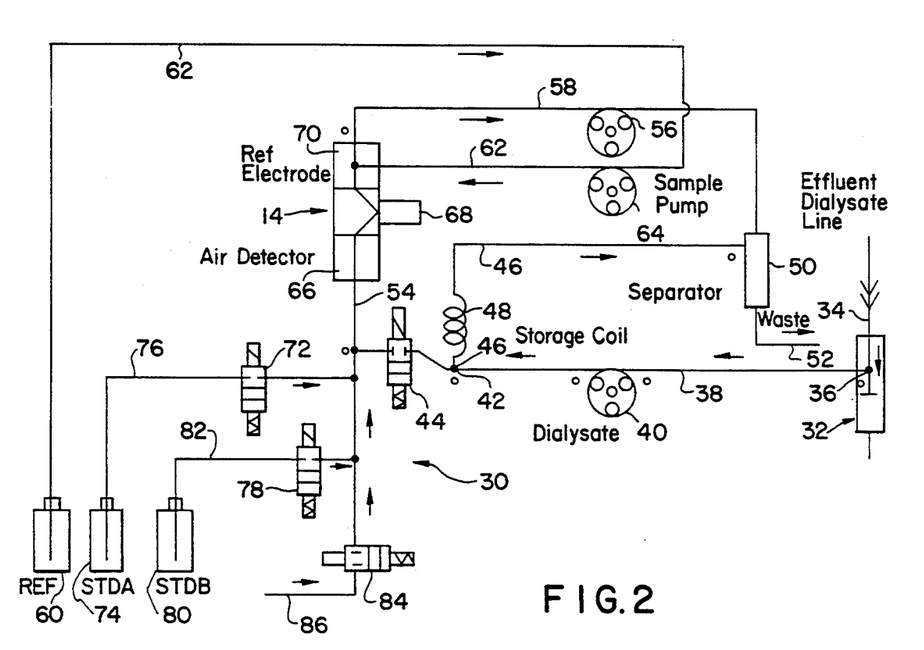
FIG. 2 is a schematic diagram of one embodiment of a fluid sampling urea input module utilized in a hemodialysis monitoring system.

At least a portion of the module 12 preferably is coupled permanently to the dialysate effluent line (as illustrated in FIG. 2). The urea sensor 14 can be an electrode sensor, such as described in U.S. Pat. No. 4,686,479, entitled *APPARATUS AND CONTROL KIT FOR ANALYZING BLOOD SAMPLE VALUES INCLUDING HEMATOCRIT*, which also is incorporated herein by reference. The liquid sample is contacted with a urea sensor that includes a urease layer associated with an electrode adapted to generate output in response to ammonium ions. The urease layer converts a portion of the urea in the sample to ammonium ions, and the ions contact the electrode to generate output related to the urea concentration in the sample.

There are other approaches to fluid sensing and any fluid marker sensor that can measure the fluid marker concentration in the effluent dialysate line can be utilized for this purpose. The invention, therefore, is not specific to a particular type of fluid marker sensor.

There are also other approaches to the flow configuration of the fluid marker sensor. The most direct configuration is location of the fluid marker sensor in the effluent dialysate stream. Another direct configuration as illustrated herein, is obtaining a sample volume from the fluid stream and flowing the sample volume to the sensor. Other configurations could include:

1. Locating the sensor in the fresh inflow dialysate stream with effluent dialysate being pumped in, upstream of the sensor, in a flow injection mode.

2. Pumping inflow and outflow streams in the desired proportions for dilution past the fluid marker sensor.

3. A flow injection scheme where a carrier buffer stream is pumped past the fluid marker sensor with injection of effluent dialysate into this buffer stream.

One urea input/sensor module embodiment of the fluid sampling input module 12 of the present invention including the urea sensor 14, is designated generally by the reference numeral 30 in FIG. 2. The module 30 includes a sample port 32, which preferably forms a part of a discharge or dialysate effluent line 34. The module 30 taps into the dialysate effluent line 34 via a junction 36 coupled to a sampling line 38.

The module 30 samples the dialysate effluent by activating a self occluding peristaltic or roller pump 40. The line 38 is coupled to a junction 42 and to a normally closed valve 44. The junction 42 also is coupled to a line 46, which includes a storage coil 48. The storage coil 48 is first filled with the dialysate effluent, with the excess dialysate effluent continuing through the line 46 to a separator 50. The separator 50 includes an air gap which prevents a backup of the dialysate effluent and also prevents an electrical short through the line 52.

Once the storage coil 48 is filled, the self occluding pump 40 is stopped, which closes the line 38 from the junction 36 to the pump 40. The valve 44 then is opened allowing the sample dialysate to flow through the valve into a line 54 and then to and through the urea sensor 14. The sample dialysate is caused to flow by a sample pump 56, which is coupled between the urea sensor 14 and the discharge separator 50 by a line 58.

For each measurement, sample dialysate preferably is input to the urea sensor 14 and flushed through the separator 50 several times to ensure a good sample value. At the same time the sample dialysate is pumped through the urea sensor 14, a reference fluid from a source 60 also is pumped into the urea sensor 14 via a line 62 and a second pump 64. The second pump 64 preferably can be a second roller head on the sample pump 56, but could also be a second pump coupled to operate at the same time as the sample pump 56.

As shown in more detail in U.S. Pat. No. 4,686,479, the urea sensor 14 includes an air detector 66 to determine if the sample dialysate is present in the urea sensor 14. The sensor 14 employs an electrode 68 with a membrane (not illustrated) which is specific to ammonium. The electrode 68 senses dialysate urea nitrogen (DUN) which is compared to a reference electrode 70. The signal generated by the urea sensor 14 then can be coupled to the urea signal analyzer 18, as will be described in more detail hereinafter.

At the beginning of the hemodialysis treatment with a patient and periodically, as desired, both a low reference standard and a high reference standard are run on the module 30 to calibrate the module 30. To calibrate the module 30 with the low standard, the valve 44 remains closed and a valve 72 is opened to allow the second pump 64 to draw in the low standard fluid from a source 74 via a line 76. The urea sensor 14 measures the low standard to develop a low standard reference point.

A high standard also is utilized in the calibration of the module 30. To run a high standard test, all the valves are closed, except for a high standard valve 78. The open valve 78 allows the second pump 64 to draw a high standard fluid from a source 80 via a line 82. The high standard fluid also is measured in the urea sensor 14 to develop a high standard reference point.

Utilizing the low and high standard reference points, a slope and intercept are determined. After the calibration procedure, the module 30 should retain the calibration for about four (4) hours which is approximately the length of time of the dialysis treatment for an individual patient. The low reference standard can be run after each procedure and as desired to insure that the module 30 has maintained calibration.

At the end of the low standard cycle, the module 30 closes the valves 44, 72 and 78 and opens an air valve 84 for a period of time, which allows the sample pump 64 to draw air into a line 86 through the valve 84, the urea sensor 14 and out the discharge line 52. This air segment between each fluid segment helps ensure that the urea sensor 14 and the lines 54 and 58 are clean and empty of any substantial amount of residual fluid.

Figure 3:
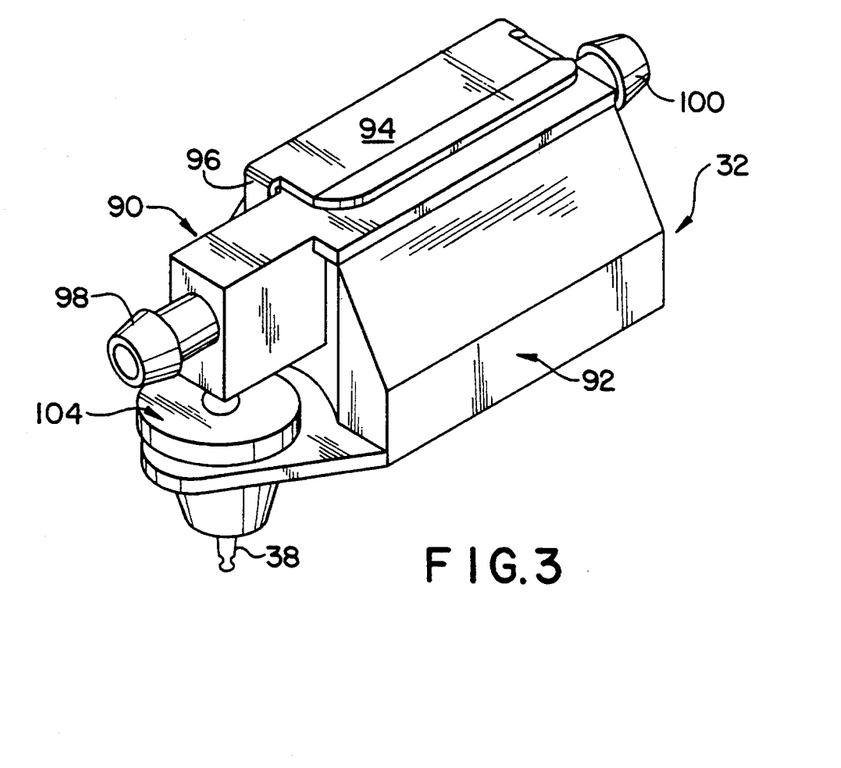
FIG. 3 is a perspective view of one embodiment of a sample port of the fluid sampling module of the present invention.
Figure 4:
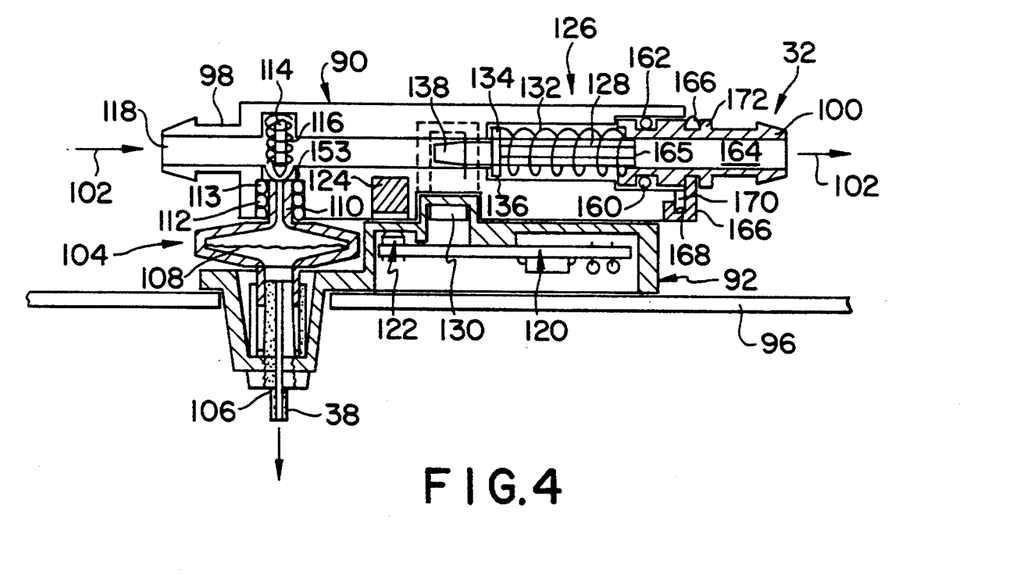
FIG. 4 is a side sectional view of the sample port of FIG. 3.
Figure 5:
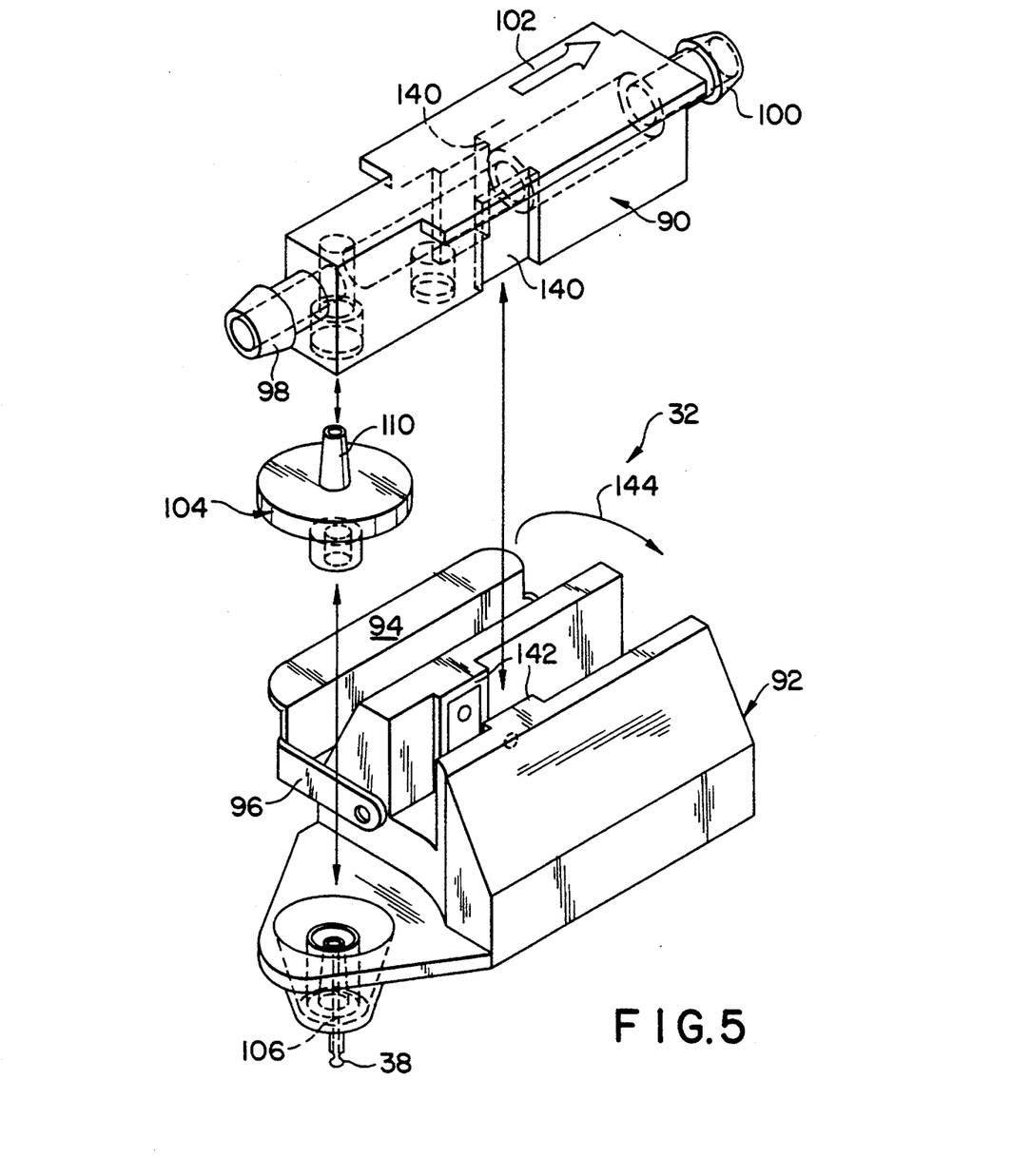
FIG. 5 is an exploded perspective view of the sample port of FIG. 3.

Referring now to FIGS. 3–5 one embodiment of the sample port 32 of the present invention is illustrated in further detail. The sample port 32 includes a flow detector body 90, which can be detachably mounted into a base or saddle 92. The body 90 is secured into the saddle 92 by a bail 94 pivotably mounted by a pair of arms 96 (only one of which is illustrated).

When the body 90 is inserted into the saddle 92, the bail 94 is pivoted to secure and engage the body 90 into the saddle 92. The saddle 92 preferably is permanently mounted to a wall 96 of the module 12 or of a hemodialysis machine (illustrated in FIG. 9). The dialysate effluent fluid flows into an inlet connector 98 and out an exit connector 100, as illustrated by the arrows 102. The inlet connector 98 would be coupled to the dialysate effluent line 34, preferably permanently, and the exit connector 100 would be coupled, preferably permanently, to an exit or waste line 103 (FIG. 2). Thus, the operation of the module 12 would not be exposed to the dialysate effluent, other than from the conventional waste line 103.

The body 90, the saddle 92 and the bail 94 are configured such that the sample port 32 is assembled and aligned and all fluid connections are made without leakage of the dialysate effluent. The saddle 92 includes a removable filter assembly 104 which is sealingly mounted onto a conventional luer lock connector 106. The filter assembly 104 is a commercial hydrophilic filter assembly, which preferably includes a 0.2 micron filter 108. The filter 108 can be a 0.2 micron filter sold by Gelman Sciences, Product No. 4192, which is a low protein binding, non-pyrogenic filter. The filter 108 prevents biological bacteria and pyrogen from passing through into the sampling line 38 which is connected to the luer lock 106.

The sample port 32 assembly is connected by a make before break type sealing arrangement. The filter assembly 104 includes an upper cylindrical inlet tube 110. As the body 90 is forced into the saddle 92 by closing the bail 94, the tube 110 first is sealed into a first O-ring 112 of a double or pair of O-rings 112 and 113, which in combination with the tube 110 form a fluid tight seal. The body 90 now is sealed to the filter assembly 104, but the dialysate effluent is still sealed in the body 90 and cannot yet flow to the filter assembly 104.

As the bail 94 continues to close, it forces the body 90 further against the saddle 92 and hence the tube 110 past the second O-ring 113. In the fully seated and sealed position, illustrated in FIG. 4, the tube 110 now has been forced against a poppet valve body 114. The tube 110 moves the body 114 against a bias spring 116 and away from the O-ring 113, thus opening an internal fluid passageway 118 in the body 90. This fully mated position allows a volume of the dialysate effluent to flow into and through the filter assembly 104 into the sampling line 38, where it can be sampled as described with respect to FIG. 2.

When the body 90 is released from the saddle 92, the reverse closing of the poppet valves occurs. The body 114 first moves back into sealing engagement with the O-ring 113, which seals the dialysate effluent into the body 90. The body 90 then is further removed from the saddle 92, which then breaks the seal between the tube 110 and the O-ring 112. The minimal priming volume of the make before break or seal before open action minimizes carryover into the filter assembly 104 and hence the line 38.

The sample port 32 also preferably includes a circuit board 120 mounted to the saddle 92. The operation of the circuit will be described in further detail with respect to FIG. 11. The circuit board 120 includes a hall effect sensor 122 mounted thereto. The sensor 122 senses a magnet 124 mounted into or onto the body 90, when the body 90 is seated into the saddle 92. The signal generated by the sensor 122 verifies that the dialysate effluent line 34 is coupled to the sampling line 38, such that the urea input module 12 is enabled to input samples from the dialysate effluent line 34.

The circuit board 120 also includes a dialysate effluent fluid flow sensing assembly 126. The flow sensor 126 includes the body 90, a flow detector plunger 128 and an optical sensor 130. The plunger 128 is mounted into the passageway 118. The plunger 128 is biased by a compression spring 132, bearing against a flange 134 formed in the plunger 128, into a minimal diametrical clearance engagement against a shoulder 136 formed in the passageway 118. The plunger 128 preferably is a rotameter-type plunger.

The flow sensor assembly 126 allows the plunger 128 to be biased for a relatively specific opening pressure which is related to a relatively specific fluid flow rate.

As an example, the plunger 128 will remain positioned with a low diametrical clearance against the shoulder 136 whenever the flow rate is less than approximately 100 ml/min. When the flow rate reaches approximately 300 ml/min, then the bias spring force will be overcome and the plunger 128 then will be forced back against the spring 132, allowing a greater volume of the dialysate to flow through the passageway 118. The flow sensor assembly 126 operates with a low pressure drop between the inlet connector 98 and the exit connector 100, for example, on the order of 20 mm of mercury at a dialysate effluent flow rate of 500 ml/min. Because of the low flow rate achievable and the ability to non-electrically detect (described further hereinafter) or sense when the dialysate flow has been bypassed or isolated from the dialyzer, the flow sensor assembly 126 can be utilized with virtually any type of hemodialysis machine.

The non-electrical flow detection is provided by the optical sensor 130 acting with the plunger 128. The optical sensor 130 can, for example, be formed by a phototransistor and an LED device. The plunger 128 includes a light path blocking tip 138. In the closed position, with the plunger 128 bearing against the shoulder 136 from the force of the spring 132, as illustrated in FIG. 4, the optical sensor 130 will have its light path blocked, which then provides a no flow signal to the urea input module 12. When the flow rate has reached a sufficient/predetermined level, preferably approximately 300 ml/min, then the plunger 128 and hence the tip 138 will be retracted from the optical path and the optical sensor 130 will provide a valid dialysate effluent flow rate signal to the urea input module 112.

Referring to FIG. 5, the alignment features of the body 90 and the saddle 92 of the sample port 32 best are illustrated. The body 90 includes a pair of alignment channels 140 on opposite sides of the body 90. The alignment channels 140 securely mate with a pair of projections 142 formed on opposite sides of the saddle 92. The alignment and engagement of the body 90 and the saddle 92 is completed and secured by pivoting the bail 94 over the top of the body 90, as indicated by an arrow 144.

The details of the body 90 and the assembly of the flow detector assembly 128 are best illustrated by FIGS. 4 and 6–8. The plunger 128 (FIG. 8) preferably is formed from an optically non-transmissive material or can at least have the tip 138 coated to block light transmission therethrough. Typically the plunger 128 can be molded from a plastic material and preferably includes four flanges 146, to minimize the pressure drop in the fluid flow path, over which the spring 152 is mounted.

Figure 6:
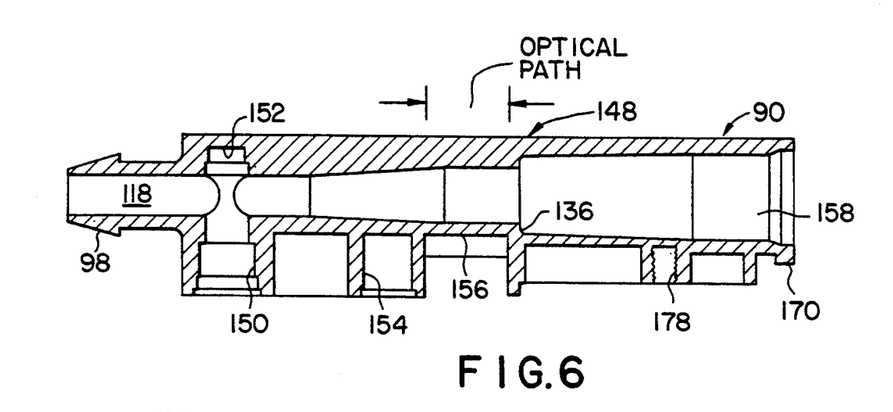
FIG. 6 is a side sectional view of the flow detector body of the sample port of FIG. 3.

The saddle 92 also can be a molded plastic material. The body 90, however, at least must include an optically transparent path or portion 148 transversely of the body 90. Preferably, the body 90 can be molded from a optically transparent material. This provides the optical path 148 as well as allowing visual inspection of the flow passageway 118 through the body 90 to monitor possible effluent blockage.

The body 90 includes a transverse passageway 150, into which is mounted the popper 114 and the O-rings 112 and 113. The transverse passageway 150 includes an end portion 152 which provides a seat for the spring 116 and clearance for the poppet 114. An end 153 of the poppet 114 normally is biased against the O-ring 113 to form a fluid seal. The magnet 124 is mounted into a recess 154 and the optical sensor 130 is mounted into a recess 156 in the body 90.

The flow sensor assembly 126 includes the outlet connector 100, which is a separate piece inserted into an enlarged portion 158 of the passageway 118. The outlet connector 100 includes a first annular recess 160 into which is seated an O-ring seal 162. The seal 162 provides a fluid seal for the outlet connector 100 when it is mounted into the portion 158 of the body 90. The outlet connector 100 also includes an internal flow passageway 164, preferably of about the same dimensions as the passageway 118 at the inlet connector 98. The plunger 128 includes a reduced size portion 165, which is sized to slidingly fit into the passageway 164.

Figure 7:
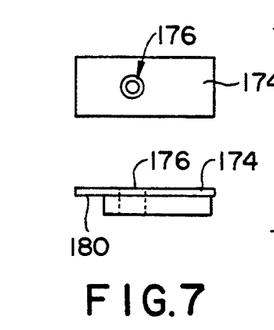
FIG. 7 is a combined top and scale view of a retainer clip of the sample port body.
Figure 8:
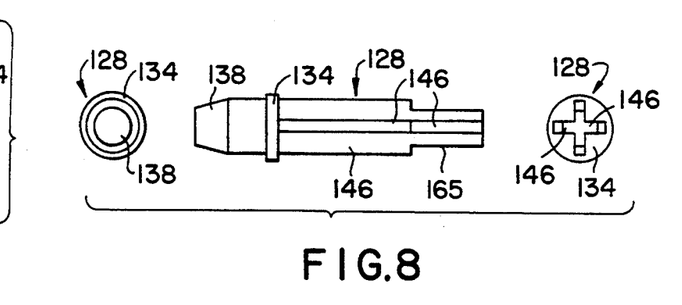
FIG. 8 is a combined end and side views of a flow detector plunger of the sample port body.

The outlet connector 100 is secured into the body 90 by any convenient securing structure, but preferably by a snap clip connector 166. The snap clip connector 166 preferably is formed of a semi-rigid plastic material, having an opening on one side (not illustrated) and having an angular groove 168. The angular groove 168 snaps over a lip 170 found at the end of the body 90 and also into a peripheral groove 172 found in the outlet connector 100. The snap clip 166 then can be retained on the outlet connector 100 and the body 90 by a retainer clamp 174 (FIG. 7). The retainer clamp 174 includes an aperture 176. The retainer clip 174 then can be secured to the body 90 by a screw (not illustrated) threaded through the aperture 176 into a threaded passageway 178 formed in the body 90. A lip 180 of the retainer clip 174 bears against and clamps the snap clip 166 onto the outlet connector 100 and the body 90. This causes the snap clip 166 to be securely retained and removable only by utilizing a tool, such as a screw driver, for safety purposes.

Figure 9:
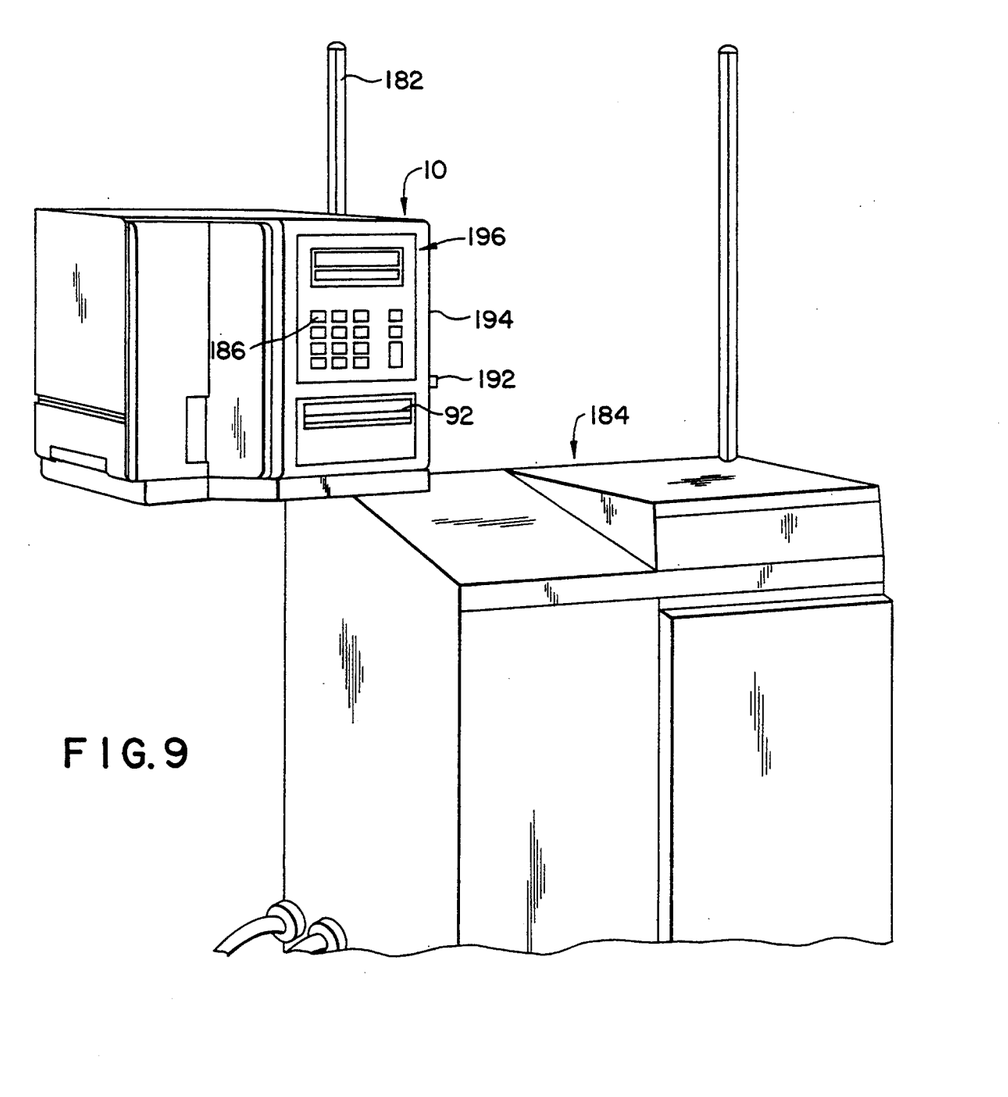
FIG. 9 is a perspective view of one hemodialysis monitoring system embodiment utilizing the fluid sampling urea input module of the present invention and illustrating one type of data input.

Referring to FIG. 9, one embodiment of a hemodialysis monitoring system 10 is mounted onto a standard 182 of a hemodialysis machine 184, such as a Model SPS-550 produced by the assignee of the present invention. The patient database can be maintained on any commercial computer (not illustrated) and the relative data then would be loaded into the hemodialysis monitoring system 10 through a serial communication port located on the rear of the system 10 (not illustrated) or can be manually entered via a keyboard 186.

Figure 10:
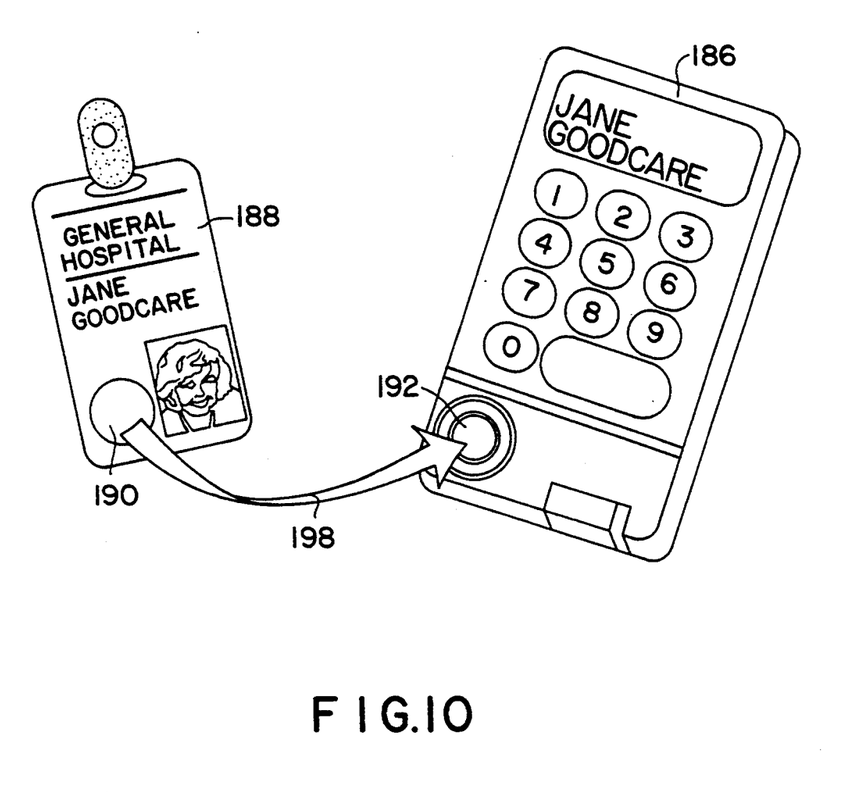
FIG. 10 is a perspective view of one embodiment of a patient ID card.

The patient preferably will have an individual ID card, which can contain merely the patient's identification. One preferable type of patient ID card is an ID card 188 (FIG. 10), which includes a data carrier 190. One button shaped type of data carrier 190 is sold by Dallas Semiconductor of Dallas, Tex. The hemodialysis monitoring system 10 can include a matching button data port 192, illustrated as being located on the keyboard 186 in FIG. 10. The button data port 192 can be located wherever desired on the hemodialysis monitoring system 10, such as on a side 194 of a cabinet 196. Utilizing the ID card 188, the patient data is transferred just by touching the button 190 to the button data port 192 as illustrated by a data transfer arrow 198. Following treatment, the data carrier card button 190 again would be touched to the button data port 192 to load the treatment information from the hemodialysis monitoring system 10 to the data carrier card button 190. The database computer also can include a data port button similar to the port 192 (not illustrated) for a like transfer of information. This eliminates keyboard entry errors.

The cabinet 196 would include the saddle 92 mounted to the front wall 96 as illustrated in FIGS. 4 and 9.

Although one specific embodiment of the hemodialysis monitoring system 10 is illustrated, the physical cabinet embodiments can vary as desired. Also, the body 92 and the associated lines are not illustrated, but the body 92 would be mounted into the saddle 92 and connected to the hemodialysis machine 184 as illustrated in FIGS. 2 and 4.

Figure 11:
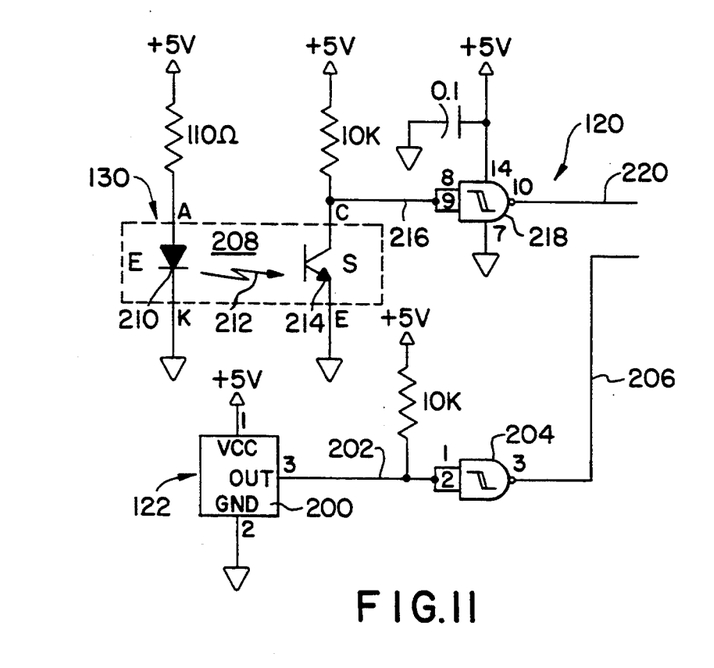
FIG. 11 is an electronic schematic diagram of one embodiment of a sample port verification and flow detector.

Referring now to FIG. 11, one embodiment of the circuitry of the circuit board 120 of the urea input module is illustrated. A conventional Hall effect sensor microchip 200 is illustrated. The microchip 200 forms the active element of the sensor 122 (FIG. 4). When the magnet 124 is moved into position by mounting the body 90 into the saddle 92, the microchip 200 generates a signal on a line 202 which is connected to a signal conditioner 204, which outputs a signal on an output line 206. The signal on the output line 206 is utilized by the urea input module 12 to verify that the body 90 is seated in the saddle 92.

The optical sensor 130 also is mounted on the circuit board 120 and includes an opto interrupter 208. The opto interrupter 208 includes an LED 210, which emits light, indicated by an arrow 212. When the tip 138 of the plunger 128 is moved out of the optical path by the dialysate effluent flow, then the light 212 can be sensed by a phototransistor 214, which then generates a signal on a line 216 connected to another signal conditioner 218, which in turn generates an output signal on a line 220. The signal on the line 220 is utilized by the urea input module 12 to verify that sufficient dialysate effluent flow is occurring through the sample port 32 to enable a valid sampling of the dialysate effluent to be collected for measurement.

We claim as our invention

1. A method of sampling fluid in a fluid line, comprising:
   providing a sample port body including a through passageway and coupling said passageway to a fluid line;
   releasably coupling said body to a separate base unit for coupling said passageway to a sampling line;
   detecting the fluid flow rate through said passageway in said body; and
   selectively enabling said sampling line when a predetermined flow rate is detected to obtain a volume of sample fluid from said fluid line, whereby sampling is conducted only when the fluid line flow rate is above a minimum value so that the sampling line flow rate is relatively low as compared to the fluid line flow rate.

2. The method as defined in claim 1 including coupling said passageway to a dialysate waste effluent line in a hemodialysis machine.

3. The method as defined in claim 2 including coupling said body to a base unit by coupling said passageway to a sampling line through a filter and filtering the dialysate effluent passing into said sampling line.

4. The method as defined in claim 1 including sealingly coupling said body to a base unit including a sampling line by first sealing said body to said base unit then coupling said passageway to said sampling line.

5. The method as defined in claim 1 including coupling said body to a base unit including coupling said passageway to a sampling line and detecting when said body is coupled to said base unit.

6. The method as defined in claim 2 including sealingly coupling said body to a base unit including a sampling line by first sealing said body to said base unit and then coupling said passageway to said sampling line.

7. The method as defined in claim 6 including coupling said body to said base unit including coupling said passageway to a sampling line and detecting when said body is coupled to said base unit.

8. The method as defined in claim 7 including coupling said body to said base unit including coupling said passageway to a sampling line through a filter and filtering the dialysate effluent passing into said sampling line.

9. An apparatus for sampling fluid line, comprising:
   means for providing a sample port body including a through passageway and means for coupling said passageway to a fluid line;
   means for releasably coupling said body to a separate base unit including means for coupling said passageway to a sampling line;
   means for detecting the fluid flow rate through a passageway and said body; and
   means for selectively enabling said sampling line when a predetermined flow rate is detected to obtain a volume of sample fluid from said fluid line, whereby sampling can be conducted only when the fluid line flow rate is above a minimum value so that the sampling flow rate is relatively low as compared to the fluid line flow rate.

10. The apparatus as defined in claim 9 including means for coupling said passageway to a dialysate waste effluent line in a hemodialysis machine.

11. The apparatus as defined in claim 10 including means for coupling said body to a base unit including means for coupling said passageway to a sampling line and means for filtering the dialysate effluent passing into said sampling line.

12. The apparatus as defined in claim 9 including means for sealingly coupling said body to a base unit including a sampling line including means for first sealing said body to said base unit and then coupling said passageway to said sampling line.

13. The apparatus as defined in claim 9 including means for coupling said body to a base unit including means for coupling said passageway to a sampling line and means for detecting when said body is coupled to said base unit.

14. The apparatus as defined in claim 10 including means for sealingly coupling said body to a base unit including a sampling line including means for first sealing said body to said base unit and then coupling said passageway to said sampling line.

15. The apparatus as defined in claim 14 including means for coupling said body to said base unit including coupling said passageway to a sampling line and means for detecting when said body is coupled to said base unit.

16. The apparatus as defined in claim 15 including means for coupling said body to said base unit including coupling said passageway to a sampling line and means for filtering the dialysate effluent passing into said sampling line.

17. A method of sampling fluid in a fluid line, comprising:
   providing a sample port body including a through passageway and coupling said passageway to a fluid line; and
   sealingly coupling said body in a releasable manner to a separate base unit including a sampling line by first sealing said body to said separate base unit, and then coupling said passageway to said sampling line, whereby sampling is conducted only when the fluid line flow rate is above a minimum value so that the sampling line flow rate is relatively low as compared to the fluid line flow rate.

18. The method as defined in claim 17 including coupling said passageway to a dialysate waste effluent line in a hemodialysis machine.

19. The method as defined in claim 18 including coupling said body to said base unit by coupling said passageway to a sampling line through a filter and filtering the dialysate effluent passing into said sampling line.

20. The method as defined in claim 17 including coupling said body to said base unit by coupling said passageway to a sampling line and detecting when said body is coupled to said base unit.

21. The method as defined in claim 17 including detecting the fluid flow rate through said fluid line and said body and enabling said sampling line when a predetermined flow rate is detected to obtain a volume of sample fluid from said fluid line.

22. The method as defined in claim 18 including detecting the fluid flow rate through said fluid line and said body and enabling said sampling line when a predetermined flow rate is detected to obtain a volume of sample fluid from said fluid line.

23. The method as defined in claim 22 including coupling said body to said base unit including coupling said passageway to a sampling line and detecting when said body is coupled to said base unit.

24. The method as defined in claim 23 including coupling said body to said base unit including coupling said passageway to a sampling line through a filter and filtering the dialysate effluent passing into said sampling line.

25. An apparatus for sampling fluid in a fluid line, comprising:
   means for providing a sample port body including a through passageway and means for coupling said passageway to a fluid line; and
   means for sealingly coupling said body in a releasable manner to a separate base unit including a sampling line including means for first sealing said body to said separate unit, and then coupling said passageway to said sampling line, whereby sampling can be conducted only when the fluid line flow rate is above a minimum value so that the sampling flow rate is relatively low as compared to the fluid line flow rate.

26. The apparatus as defined in claim 25 including means for coupling said passageway to a dialysate waste effluent line in a hemodialysis machine.

27. The apparatus as defined in claim 26 including means for coupling said body to said base unit including means for coupling said passageway to a sampling line and means for filtering the dialysate effluent passing into said sampling line.

28. The apparatus as defined in claim 25 including means for coupling said body to said base unit including means for coupling said passageway to a sampling line and means for detecting when said body is coupled to said base unit.

29. The apparatus as defined in claim 25 including means for detecting the fluid flow rate through said fluid line and said body and means for enabling said sampling line when a predetermined flow rate is detected to obtain a volume of sample fluid from said fluid line.

30. The apparatus as defined in claim 26 including means for detecting the fluid flow rate through said fluid line and said body and means for enabling said sampling line when a predetermined flow rate is detected to obtain a volume of sample fluid from said fluid line.

31. The apparatus as defined in claim 30 including means for coupling said body to said base unit including means for coupling said passageway to a sampling line and means for detecting when said body is coupled to said base unit.

32. The apparatus as defined in claim 31 including means for coupling said body to said base unit including means for coupling said passageway to a sampling line and means for filtering the dialysate effluent passing into said sampling line.

33. A method of sampling fluid in a fluid line, comprising:
   providing a sample port body including a through passageway and coupling said passageway to a fluid line;
   releasably coupling said body to a separate base unit including coupling said passageway to a sampling line;
   detecting when said body is coupled to said separate base unit;
   detecting the fluid flow rate through said passageway and said body; and
   selectively enabling said sampling line when said body is detected as being coupled to said separate base unit and when a predetermined flow rate is detected, to obtain a volume of sample fluid from said fluid line, whereby sampling is conducted only when the fluid line flow rate is above a minimum value so that the sampling line flow rate is relatively low as compared to the fluid line flow rate.

34. The method as defined in claim 33 including coupling said passageway to a dialysate waste effluent line in a hemodialysis machine.

35. The method as defined in claim 34 including coupling said body to said base unit by coupling said passageway to a sampling line through a filter and filtering the dialysate effluent passing into said sampling line.

36. The method as defined in claim 33 including sealingly coupling said body to said base unit including a sampling line by first sealing said body to said base unit and then coupling said passageway to said sampling line.

37. The method as defined in claim 33 including detecting the fluid flow rate through said fluid line and said body and enabling said sampling line when a predetermined flow rate is detected to obtain a volume of sample fluid from said fluid line.

38. The method as defined in claim 34 including sealingly coupling said body to said base unit including a sampling line by first sealing said body to said base unit and then coupling said passageway to said sampling line.

39. The method as defined in claim 38 including detecting the fluid flow rate through said fluid line and said body and enabling said sampling line when a predetermined flow rate is detected to obtain a volume of sample fluid from said fluid line.

40. The method as defined in claim 39 including coupling said body to said base unit including coupling said passageway to a sampling line through a filter and filtering the dialysate effluent passing into said sampling line.

41. An apparatus for sampling fluid in a fluid line, comprising:

a sample port body including a through passageway and means for coupling said passageway to a fluid line;

means for releasably coupling said body to a separate base unit including means for coupling said passageway to a sampling line;

means for detecting when said body is coupled to said separate base unit;

means for detecting the fluid flow rate through said passageway and said body; and means for selectively enabling said sampling line when said body is coupled to said separate base unit and a predetermined flow rate is detected in said fluid line for obtaining a volume of sample fluid from said fluid line, whereby sampling can be conducted only when the fluid line flow rate is above a minimum value so that the sampling flow rate is relatively low as compared to the fluid line flow rate.

42. The apparatus as defined in claim 41 including means for coupling said passageway to a dialysate waste effluent line in a hemodialysis machine.

43. The apparatus as defined in claim 42 including means for coupling said body to said base unit including means for coupling said passageway to a sampling line and means for filtering the dialysate effluent passing into said sampling line.

44. The apparatus as defined in claim 41 including means for sealingly coupling said body to said base unit including a sampling line including means for first sealing said body to said base unit and then coupling said passageway to said sampling line.

45. The apparatus as defined in claim 41 including means for detecting the fluid flow rate through said fluid line and said body and means for enabling said sampling line when a predetermined flow rate is detected to obtain a volume of sample fluid from said fluid line.

46. The apparatus as defined in claim 42 including means for sealingly coupling said body to said base unit including a sampling line including means for first sealing said body to said base unit and then coupling said passageway to said sampling line.

47. The apparatus as defined in claim 46 including means for detecting the fluid flow rate through said fluid line and said body and means for enabling said sampling line when a predetermined flow rate is detected to obtain a volume of sample fluid from said fluid line.

48. The apparatus as defined in claim 47 including means for coupling said body to said base unit including means for coupling said passageway to a sampling line and means for filtering the dialysate effluent passing into said sampling line.

* * * * *